US010518023B2

(12) United States Patent
Archilla et al.

(10) Patent No.: US 10,518,023 B2
(45) Date of Patent: Dec. 31, 2019

(54) MEDICAL INJECTION DEVICE WITH TELESCOPICALLY MOVABLE NEEDLE SHIELD HAVING A CLEANING CHAMBER FOR THE NEEDLE

(71) Applicant: Novo Nordisk A/S, Bagsvaerd (DK)

(72) Inventors: Ruben Archilla, Copenhagen (DK); Morten Soerensen, Ballerup (DK); Morten Revsgaard Frederiksen, Copenhagen (DK); Mattias Ingerslev, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 123 days.

(21) Appl. No.: 15/567,830

(22) PCT Filed: Apr. 20, 2016

(86) PCT No.: PCT/EP2016/058722
§ 371 (c)(1),
(2) Date: Oct. 19, 2017

(87) PCT Pub. No.: WO2016/173895
PCT Pub. Date: Nov. 3, 2016

(65) Prior Publication Data
US 2018/0117240 A1    May 3, 2018

(30) Foreign Application Priority Data

Apr. 28, 2015   (EP) .................................... 15165464

(51) Int. Cl.
*A61M 5/00*   (2006.01)
*A61M 5/315*   (2006.01)
(Continued)

(52) U.S. Cl.
CPC .......... *A61M 5/001* (2013.01); *A61M 5/2033* (2013.01); *A61M 5/2466* (2013.01);
(Continued)

(58) Field of Classification Search
CPC .. A61M 2005/2474; A61M 2005/3267; A61M 5/001; A61M 5/20; A61M 5/2033;
(Continued)

(56) References Cited

U.S. PATENT DOCUMENTS

| | | | |
|---|---|---|---|
| 3,354,881 A | 11/1967 | Bloch | |
| 4,416,663 A * | 11/1983 | Hall | ...................... A61M 5/326 |
| | | | 604/198 |

(Continued)

FOREIGN PATENT DOCUMENTS

| | | |
|---|---|---|
| DE | 102005056172 A1 | 7/2007 |
| WO | 2014029018 A1 | 2/2014 |

(Continued)

*Primary Examiner* — Brandy S Lee
(74) *Attorney, Agent, or Firm* — Wesley Nicolas (57) ABSTRACT

The invention relates to a pre-filled injection device for apportioning set dose of a liquid drug. The housing of the pre-filled injection device internally supports a non-replaceable cartridge (160) having an hollow interior containing a liquid preservative containing drug and externally supporting a removable protective cap (150). The piston rod drive system of the injection device comprises a piston rod abutting a plunger provided inside the cartridge. A needle cannula (130) having a distal part with a distal tip and an opposite proximal part and a lumen there between is insertable into the cartridge. A telescopically movable (110) shield movable from an extended position covering at least the distal tip of the needle cannula to a retracted position exposing at least the distal tip of the needle cannula is further provided. The telescopically movable shield carries a cleaning chamber (120) able to contain a quantum of the liquid preservative containing drug for cleaning at least the distal tip of the needle cannula between subsequent injections. The quantum of the liquid preservative containing drug contained in the hollow interior of the cartridge is transferred to the cleaning chamber through the lumen of the needle (Continued)

cannula by moving the cartridge axially in relation to the plunger by use of a transfer assembly.

10 Claims, 10 Drawing Sheets

(51) Int. Cl.
*A61M 5/32* (2006.01)
*A61M 5/20* (2006.01)
*A61M 5/24* (2006.01)

(52) U.S. Cl.
CPC .... *A61M 5/31501* (2013.01); *A61M 5/31583* (2013.01); *A61M 5/3202* (2013.01); *A61M 5/326* (2013.01); *A61M 5/3271* (2013.01); *A61M 5/3293* (2013.01); *A61M 5/20* (2013.01); *A61M 2005/2474* (2013.01); *A61M 2005/3267* (2013.01)

(58) Field of Classification Search
CPC ............ A61M 5/2466; A61M 5/31501; A61M 5/31583; A61M 5/3202; A61M 5/326; A61M 5/3271; A61M 5/3293
See application file for complete search history.

(56) References Cited

U.S. PATENT DOCUMENTS

| | | |
|---|---|---|
| 4,507,118 A | 3/1985 | Dent |
| 4,666,436 A | 5/1987 | McDonald et al. |

FOREIGN PATENT DOCUMENTS

| | | |
|---|---|---|
| WO | 2014064100 A1 | 5/2014 |
| WO | 2014125067 A1 | 8/2014 |
| WO | 2015062845 A1 | 5/2015 |

* cited by examiner

Fig. 17 though the movement of the hub carrying the arms are purely axial, the arms needs to be extremely precise in length which is a major drawback as the moulding tolerances then needs to be very narrow.
MEDICAL INJECTION DEVICE WITH TELESCOPICALLY MOVABLE NEEDLE SHIELD HAVING A CLEANING CHAMBER FOR THE NEEDLE

CROSS-REFERENCE TO RELATED APPLICATIONS

This application is a 35 U.S.C. § 371 National Stage application of International Application PCT/EP2016/058722 (published as WO 2016/173895), filed Apr. 20, 2016, which claims priority to European Patent Application 15165464.7, filed Apr. 28, 2015; the contents of which are incorporated herein by reference.

THE TECHNICAL FIELD OF THE INVENTION

The invention relates to a medical injection device for injecting a liquid drug and especially to a pre-filled injection device for apportioning a number of individual settable doses. The invention especially relates to such pre-filled injection device wherein the same needle cannula is used for multiple injections and wherein the tip of the needle cannula is cleaned between subsequent injections.

DESCRIPTION OF RELATED ART

Injection devices wherein the tip of the needle cannula is maintained in a cleaning solvent between subsequent injections are disclosed in U.S. Pat. Nos. 3,354,881, 4,416,663, 4,507,118 and in 4,666,436. As can be seen from these prior art injection devices, the cleaning chamber is usually carried distally on a retractable shield covering the tip of the needle cannula between subsequent injections.

Further WO2014/064100 discloses a pre-filled disposable injection device which has a telescopically shield covering the distal tip of the needle cannula between subsequent injections.

This telescopically shield is urged into a distal covering position by a spring. Further, in one embodiment, the shield is provided with a hollow chamber containing a liquid solvent such as a chemical disinfectant or biocide which cleans the tip of the needle cannula between subsequent injections.

Examples on such cleaning solvents are provided in WO 2014/029018. However, as disclosed in WO 2015/062845 it is preferred to use the preservative contained in the liquid drug as the cleaning solvent. This is preferably done by filling the cleaning chamber with preservative containing liquid drug directly from the cartridge embedded in the pre-filled injection device and thereby use a quantum of the preservative containing liquid drug as the cleaning solvent.

The filling of the cleaning chamber from the cartridge is in WO 2015/062845 done by having the protective cap coupled to the injection device such that at least the distal part of the injection device including the cartridge is forced to move proximally whenever the user rotates the protective cap.

Figures 7, 8:
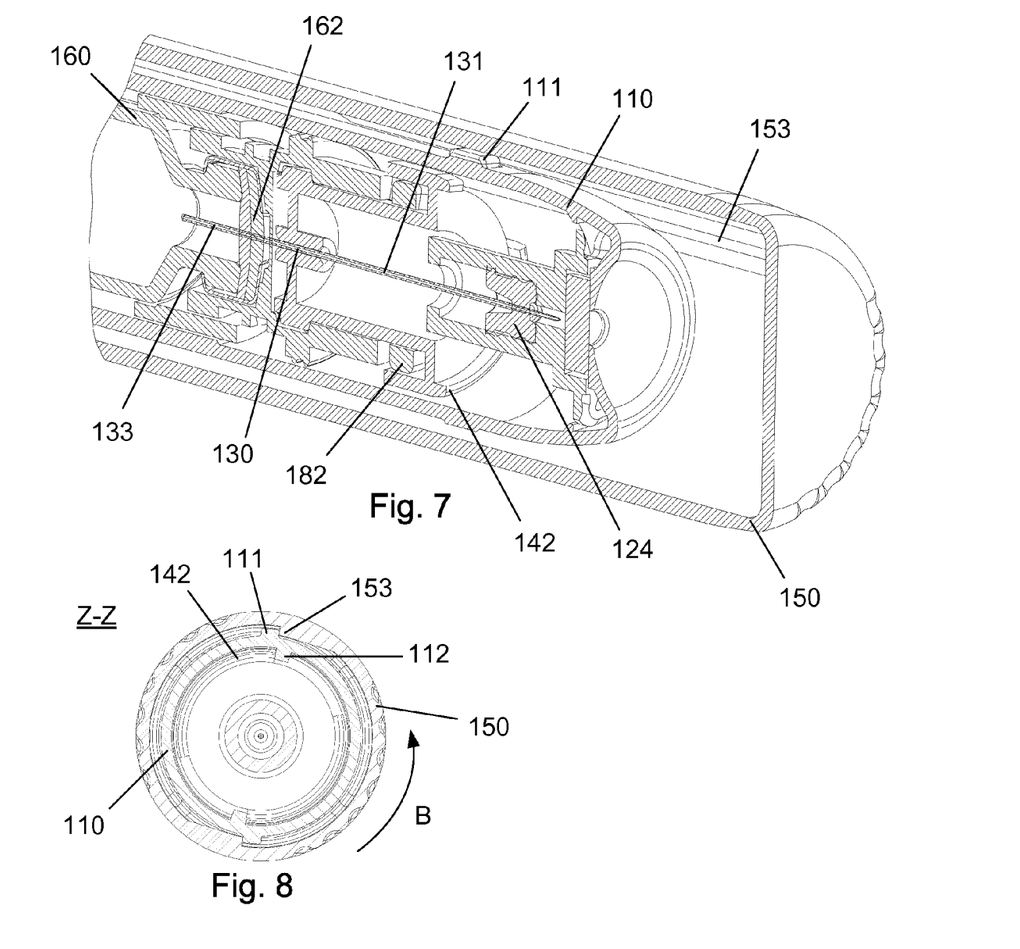
FIG. 7 show a perspective view of injection device with the proximal part of the needle cannula inserted into the cartridge.
FIG. 8 show a cross-sectional view of the injection device through the line Z-Z in FIG. 5A.
Figure 9:
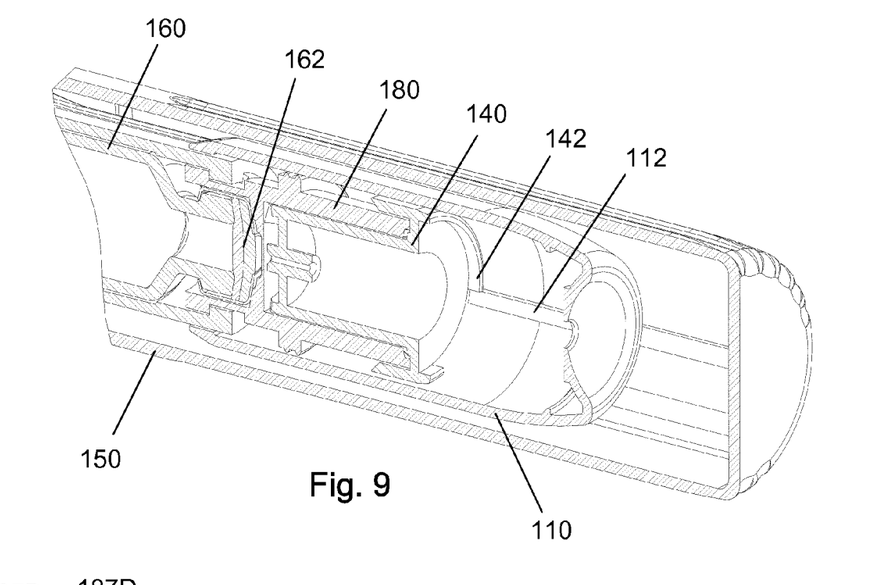
FIG. 9 show a view as in FIG. 7 with the needle cannula and the cleaning chamber removed for visual purposes.

In the embodiment disclosed in FIG. 8 and FIG. 9, the needle hub pushes the cartridge in the proximal direction when the hub is moved axially. This axial movement is transferred directly from the hub to the cartridge via a plurality of small arms provided on the needle hub which arms abuts against the top of the cartridge and thus moves the cartridge in the proximally direction.

The use of such small plastic arms extending axially has some drawbacks. One being that small arms easily break off which potentially could hinder the user in taking the injection device into use.

Further, the volume of the liquid that needs to be transferred to the cleaning chamber is rather limited while only a very little axial movement of the cartridge is required. However, since the movement of the hub carrying the arms are purely axial, the arms needs to be extremely precise in length which is a major drawback as the moulding tolerances then needs to be very narrow.

DESCRIPTION OF THE INVENTION

It is henceforth an object of the present invention to provide a motion transfer mechanism which overcomes these drawbacks.

Accordingly, in one aspect of the present invention, a pre-filled injection device for apportioning set dose of a liquid drug is provided.

This injection device comprises:

A housing which distally supports a removable protective cap such that a user can remove the protective cap before to making an injection and which housing proximally contains or supports a piston drive system. The removable cap is further rotatable in relation to the housing when mounted there upon.

A non-replaceable cartridge which is permanently embedded in the housing to form a pre-filled injection device. The interior of the cartridge contains a liquid drug in which a preservative is disposed. The cartridge has a movable plunger with a proximal surface abutting a piston rod drive system which system further has a piston rod for moving the plunger forward i.e. in the distal direction inside the cartridge A needle cannula or hollow needle tube having a distal part with a distal tip for penetrating the skin of the user, an opposite proximal part and a lumen there between, A telescopically movable shield movable from an extended position in which the shield covers at least the distal tip of the needle cannula to a retracted position in which at least the distal tip of the needle cannula is exposed to perform an injection. The telescopically movable shield further carries a cleaning chamber arranged to contain a cleaning solvent for cleaning at least the distal tip of the needle cannula between subsequent injections.

The cleaning solvent contained inside the cleaning chamber is identical to the liquid preservative containing drug contained in the interior of the cartridge and is filled into the cleaning chamber through the lumen of the needle cannula by moving the movable plunger and the cartridge relatively to each other.

In order to perform this relative movement a transfer assembly is provided which transfer assembly transfers a rotation of the protective cap to an axial displacement of the cartridge in the proximal direction. The plunger is further prevented from moving in the proximal direction. The result being that the cartridge travels proximally while the plunger remains in its position such that a quantum of the liquid preservative containing drug inside the cartridge is expelled through the lumen of the needle cannula and into the cleaning chamber.

The transfer assembly is thus rotatable arranged such that rotation of the protective cap and the transfer assembly is transplanted to an axial movement of the cartridge through rotation of the transfer assembly.

The cartridge is thus displaced in the proximal direction whereas the plunger is maintained in its position such that a relative movement is created.

In a further aspect, the transfer assembly comprises a transfer element engaging a hub. The hub preferably carries the needle cannula. Preferably, the hub has an anchoring part with a through-going hole in which hole the needle cannula is carried. The needle cannula is preferably permanently connected to the hub e.g. by gluing or the like.

The transfer element and the hub are in an aspect coupled together by a threaded connection which makes it possible to rotate the hub and the transfer element relatively to each other.

If e.g. the hub rotates relatively to the transfer element the hub and thus the needle cannula can be arranged to travel axially in relation to the transfer element. This can e.g. be used to move the needle cannula proximally in relation to the cartridge such that the proximal part of the needle cannula can be penetrated through the septum of the cartridge whenever the hub is rotated helically in the proximal direction relatively to the transfer element.

The hub is preferably rotated by the user rotating the protective cap which is preferably threaded to the housing such that the user is required to rotate the protective cap in order to remove it prior to executing an injection. In one aspect, the protective cap is provided with means for translation rotation of the protective cap to a rotation of the shield which further translate rotation to the hub. Hence, the shield rotates together with the protective cap. The shield is further guided helically in a proximal direction such that the shield moves axially in a helical movement when rotated. The result being that as the user rotates the protective cap both the shield and the hub rotates simultaneously and moves helically in the proximal direction such that the proximal part of the needle cannula penetrates through the septum of the cartridge and the distal tip of the needle cannula which also move axially remains inserted in the cleaning chamber.

The threaded connection between the hub and the transfer element preferably has the same pitch as the thread guiding the shield proximally thereby securing that the tip of the needle cannula remains in the same relative position inside the cleaning chamber as both the hub and the cleaning chamber move proximally.

The rotation of the hub is further canalized into a rotation of the transfer element. Once the hub reaches a position in which the proximal part of the needle cannula has penetrated the septum of the cartridge, the hub rotationally engages with the transfer element such that the transfer element rotate together with the hub at the remaining part of the threaded connection.

The drive train is as follows; the protective cap translates rotation to the shield, the shield translates rotation to the hub and the hub translates rotation to the transfer element at least at the last part of its rotation. As a result, rotation of the protective cap rotates the shield, the hub and finally the transfer element. The means translating the rotation between these elements are preferably various protrusions, tracks, cams or ridges.

In a further aspect, the transfer element is coupled to the housing or a housing part via helical moving means such that once the transfer element is rotated it travels helically in the proximal direction. The helical moving means preferably comprises a protrusion engaging a helical formed track. In a preferred embodiment, the protrusion is provided as an inwardly pointing protrusion on a housing part and the track is provided as a groove-like track on an outer surface of the transfer element. However, the reversed positions could easily be arranged.

The housing part carrying the protrusion or alternatively the helical track is preferably a tube-like structure firmly connected to the housing or moulded as a part of the housing.

The transfer element abuts the cartridge such that helical movement of the transfer element is conveyed to an axial movement of the cartridge in the proximal direction. The slope of the interface between the protrusion and the helical track decides how far axially the cartridge is pushed during the rotation. In an alternative embodiment more than one protrusion and more than one helical track can be provided.

The track guiding the transfer element can in one example be formed with a plurality of steps such that the transfer element can be moved in a stepwise configuration.

The slope leading from one step to the next consecutive step is preferably formed relatively steep such that the transfer element is accelerated during the relative rotation. Such rapid acceleration of the transfer element and thus the cartridge has proven to be very beneficial in order to release the plunger from the glass of the cartridge as the plunger when made from rubber has a tendency to stick to the glass.

However, as the transfer element and the cartridge are accelerated a pressure is build up inside the cartridge since the plunger remains in its position during this sudden acceleration. This pressure can henceforth be higher than what is actually needed to pump the proper amount of the liquid drug into the cleaning chamber.

If the cartridge remains pressurized after the cleaning chamber has been filled, liquid drug will flow from the lumen of the needle cannula once the tip of the needle cannula penetrates out from the distal barrier of cleaning chamber.

This can however be avoided by sloping the guiding track a distance in the opposite direction to release the pressure introduced to release the plunger from the cartridge. This return distance is preferably smaller than the distance used to accelerate the cartridge.

During axial movement of the cartridge, the plunger inside the cartridge is proximally supported by the piston rod e.g. with a piston rod foot located between the piston rod and the plunger.

Usually in a pre-filled injection device the piston rod is prevented from movement in a proximal direction e.g. by a one-way ratchet interface. This secures that the piston rod (or the piston rod foot, if such is used) does not loose contact with the plunger.

When the plunger is prevented from proximal movement and the cartridge is urged in the proximal direction the relative movement between the cartridge and the plunger reduces the volume of the interior of the cartridge holding the preservative containing liquid drug which is then forced through the lumen of needle cannula. With the tip of the needle cannula being disposed in the cleaning chamber, the volume forced out of the cartridge flows directly into the cleaning chamber thus filling the cleaning chamber.

The cleaning chamber preferably has a variable volume which is expanded as the chamber is filled. In a preferred embodiment the cleaning chamber comprises a movable piston operating inside the chamber.

The piston travelling inside the cleaning chamber is preferably made from the material usually used for constructing septums for cartridges. This well-known material is a rubber composition which is inert to the liquid drug and the preservatives contained in the cartridge. The same material is also preferred for the distal septum of the cleaning chamber.

In operation, the hub is preferably provided with locking means locking the hub to the transfer element once the proximal part of the needle cannula is correctly penetrated into the cartridge, such that the proximal part cannot be removed once inserted. The transfer element could also be provided with means preventing rotation of the transfer element and thus the cartridge until the hub has been moved into position such that the proximal part of the needle cannula is penetrated into the cartridge before the cartridge is pushed proximally to avoid that air is sucked into the cleaning chamber.

Further, in operation, the shield is urged into its extended position by a compression spring such that the distal tip of the needle cannula is maintained inserted into the cleaning chamber between injections.

Since the injection device is a pre-filled injection device, i.e an injection device in which the cartridge cannot be replaced, it is discarded once the content of the cartridge has been used. The needle cannula which have the same lifetime as the injection device i.e. the same needle cannula is used for multiple injections, are discarded together with the pre-filled injection device.

Further, the injection device can be any kind of known injection device, manually or automatic. When automatic, the injection device can be driven e.g. by an electric motor or by a spring. If the injection device is spring driven, the spring can be released by a separate button or by the proximal movement of the telescopic shield. The spring used to expel the preservative containing drug from the cartridge is preferably a torsion spring.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and preferably connected to a hub made from a suitable material e.g. a polymer. A needle cannula could however also be made from a polymeric material or a glass material.

As used herein, the term "drug" is meant to encompass any drug-containing flowable medicine capable of being passed through a delivery means such as a hollow needle cannula in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using duralbe injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism provided either on the surface of the housing or at the proximal end of the injection device to release—fully or partially—the force accumulated in the spring when carrying out the injection.

The term "Permanently connected" or "permanently embedded" as used in this description is intended to mean that the parts, which in this application is embodied as a cartridge permanently embedded in the housing, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

Figures 5, 5A:
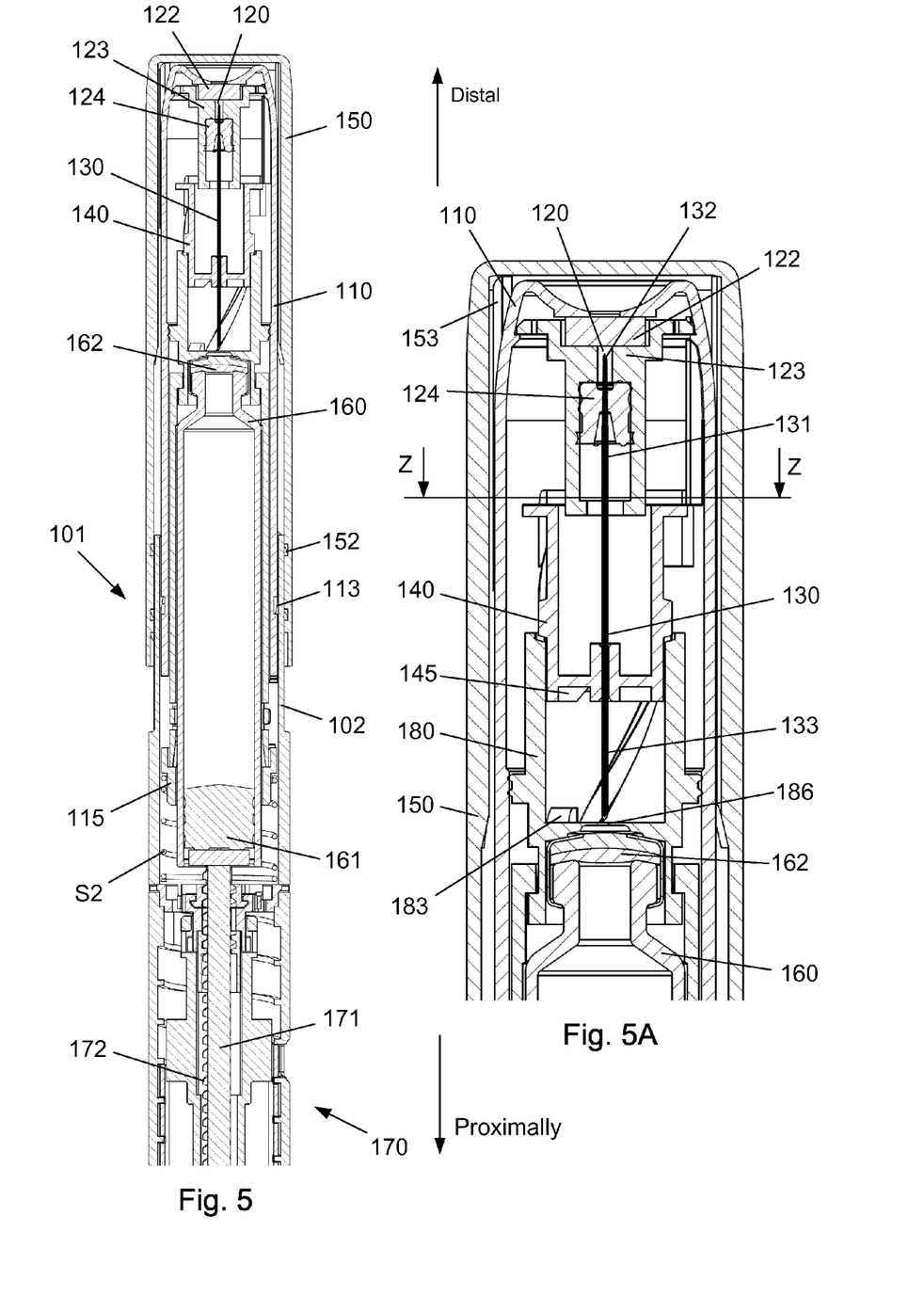
FIG. 5-5A show a cross sectional view of an embodiment of the injection device in a stored condition.

In that context it may be convenient to define that the term "distal end" in the appended figures is meant to refer to the end of the injection device pointing towards the user during injection as indicated in FIG. 5, whereas the term "proximal end" is meant to refer to the opposite end usually carrying the dose dial button. Distal and proximal is meant to be along an axial orientation extending along the longitudinal axis of the injection device.

Figure 1:
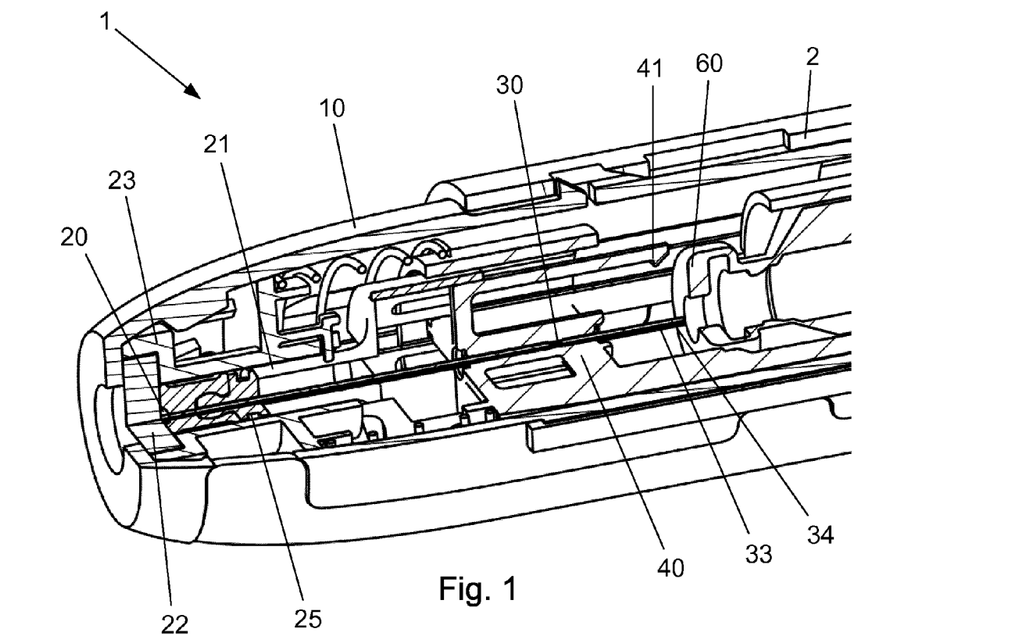
FIG. 1 shows a cut-open view of a first example of an injection device
Figure 2:
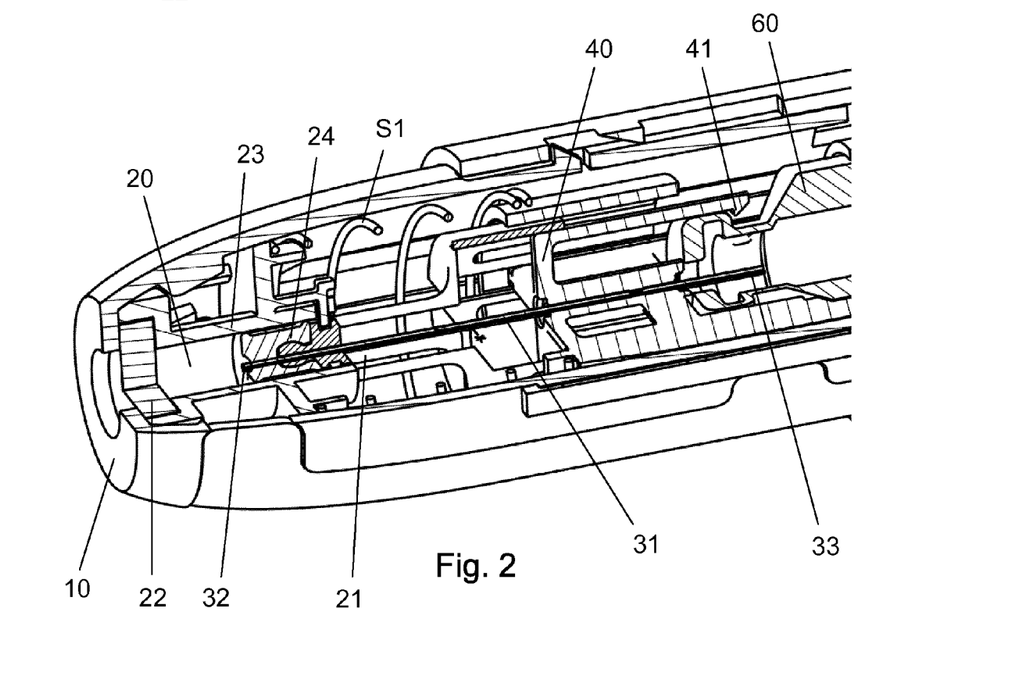
FIG. 2 shows a cut-open view of the injection device of FIG. 1 with the cleaning chamber filled.

FIG. 1 and FIG. 2 discloses an example of a pen-shaped injection device 1 with a housing 2 in which a shield 10 is slidable mounted as disclosed in WO 2015/062845. The slidable shield 10 carries a cleaning chamber 20 for cleaning the tip 32 of the needle cannula 30 between injections. The housing 2 of the injection device 1 further secures a cartridge 60 containing the liquid drug to be injected.

The needle cannula 30 is secured in a hub 40 which is movable from a first position depicted in FIG. 1 to a second position depicted in FIG. 2. The needle cannula 30 has a distal part 31 with a distal tip 32 extending in the distal direction from the hub 40 and a proximal part 33 extending in the opposite proximal direction. A lumen 34 extends through the needle cannula 30 along the axial direction.

The cleaning chamber 20 is essentially made up from two parts 21, 23 which are telescopically movable in relation to each other. The inner part 21 is distally provided with a piston 24 and the outer part 23 is permanently attached to the shield 10 e.g. by being moulded integral with the shield 20.

In one example, the outer part 23 is a separate part permanently attached to the shield 10. When the outer part 23 is formed as a separate part it can be moulded from a different material (from the shield 10) e.g. a material optimized for being in contact with the cleaning solvent contained inside the cleaning chamber 20. As an alternative to being a separate part, the outer part 23 can be moulded together with shield 10 in a 2K moulding, e.g. in a 2K moulding with different materials.

In FIG. 1 the inner part 21 is in its initial position abutting the distal septum 22 (via the piston 24) and the volume of the cleaning chamber 20 is thus rather small as it is formed as a carved-out part of the piston 24. In FIG. 2, the inner part 21 is slided axially in the proximal direction to increase the volume of the cleaning chamber 20.

FIG. 1 discloses the injection device 1 in the storage condition. The proximal end 33 of the needle cannula 30 is located distally to the cartridge 60 and no flow has been established. When the user initiates first use of the injection device 1 a not-shown mechanism moves the hub 40 in the proximal direction into the position disclosed in FIG. 2. The inner part 21 is slidable relatively to the hub 40 but coupled to the hub 40 to follow the proximal movement of the hub 40. The inner part 21 is thus pulled proximally by the hub 40 and the volume of the cleaning chamber 20 is increased.

The inner part 21 is distally constructed to carry a piston 24 which slides inside the outer part 21. Distally the cleaning chamber 20 is bordered by a distal septum 22 through which the distal part 32 of the needle cannula 30 penetrates during injection.

As the inner part 21 together with the piston 24 slides axially in the proximal direction a vacuum is created inside the cleaning chamber 20. The vacuum is growing as the cleaning chamber 20 is increased in volume. The vacuum sucks liquid drug from the cartridge 60 and into the cleaning chamber 20 through the lumen 34 of the needle cannula 30 as the proximal part 33 of the needle cannula 30 is penetrated into the cartridge 60.

In FIG. 2, the injection device 1 is ready to perform an injection. The hub 40 and the inner part 21 have moved proximally together and the hub 40 is now locked to the cartridge 60 by engaging means 41 securing the hub 40 axially. Further, the inner part 21 is locked to the outer part 23 via a locking groove 25 engaging the outer part 23 such that the inner part 21 and the outer part 23 moves axially together and relatively to the locked hub 40 whenever the shield 10 is moved.

The result being that the proximal end 33 of the needle cannula 30 hereafter remains penetrated into the interior of the cartridge 60 and the cleaning chamber 20 hereafter has a constant volume which is filled with liquid drug. Multiple injections can hereafter be performed and the compression spring S1 urges the shield 10 in the distal direction such that the distal tip 32 of the needle cannula 30 is maintained inside the now filled cleaning chamber 20 between subsequent injections.

Figures 3, 4:
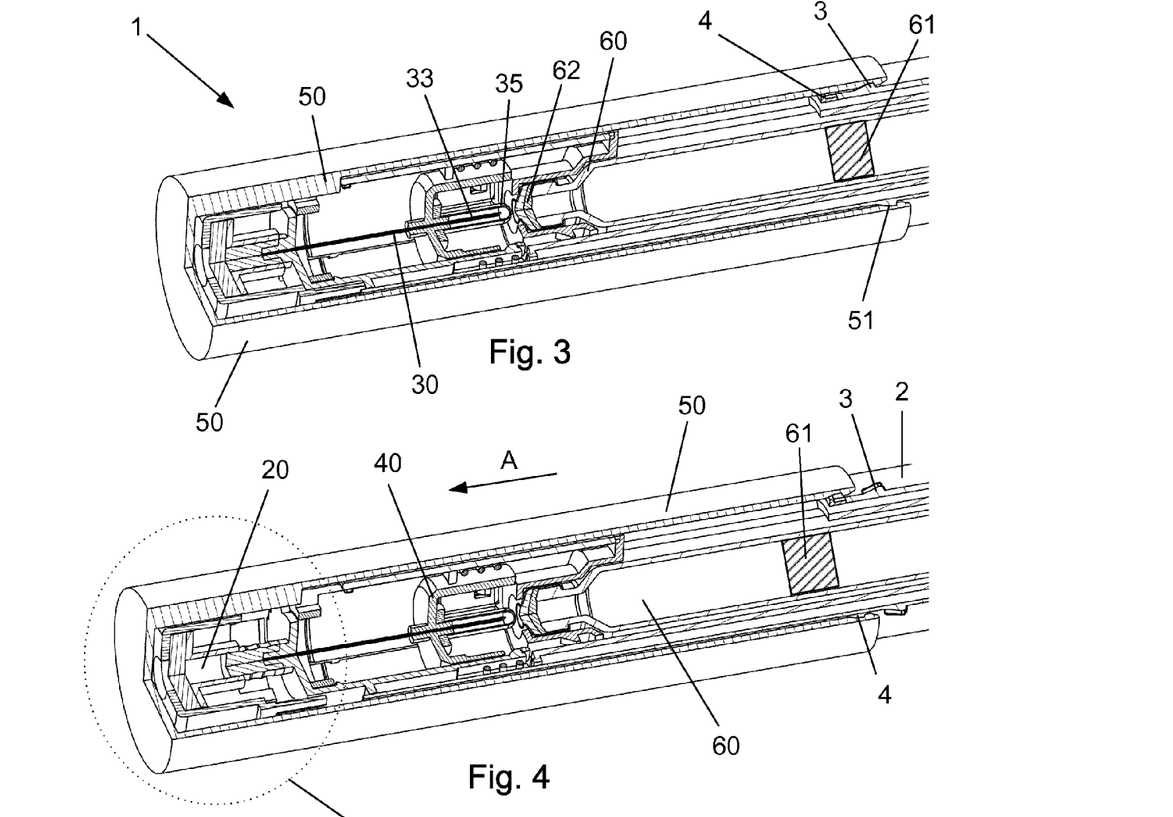
FIG. 3 shows a cut-open view of a second example of an injection device.
FIG. 4-4A shows a cut-open view of the injection device of FIG. 3 with the cleaning chamber filled.
Figure 4A:
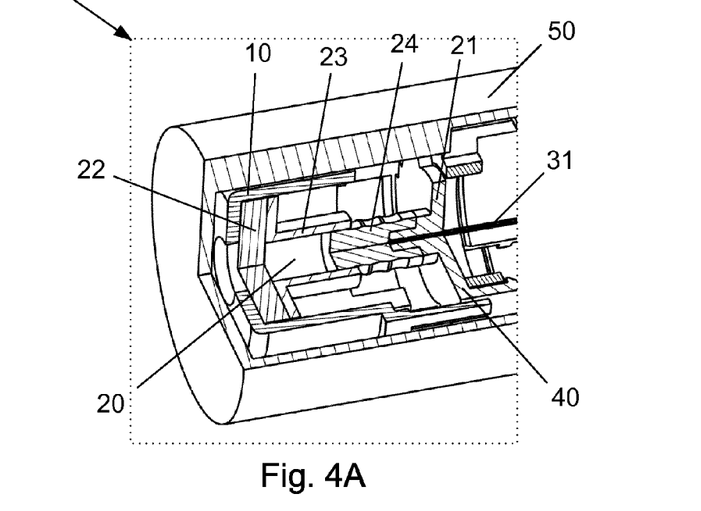

A different embodiment is disclosed in FIG. 3 and in FIG. 4-4A wherein the same numeral numbers are used for the same elements. FIG. 4A is an enlarged view of the circled part of FIG. 4.

The liquid drug is contained in the interior of the cartridge 60 which is proximally closed by a movable plunger 61 and distally sealed by a pierceable septum 62 to be pierced by the needle cannula 30. In FIG. 3 and FIG. 4 the proximal part 33 of the needle cannula 30 is located distal to the cartridge 60 such that liquid communication has not yet been established.

The proximal part 33 of the needle cannula 30 is preferably maintained sterile in a polymeric bag 35.

FIG. 3 discloses the injection device 1 in the storage condition wherein the distal part of the injection device 1 is covered by a protective cap 50. This cap 50 is proximally provided with an internal circumferential groove 51 which locks over a ridge 3 provided externally on the housing 2.

Distally the cleaning chamber 20 is provided between an inner part 21 carrying a piston 24 and an outer part 23 secured to the shield 10. Distally the cleaning chamber 20 is bordered by a distal septum 22.

When the user pulls off the cap 50 to initiate an injection as indicated by the arrow "A" in FIG. 4, the shield 10 is press fitted interior in the cap 50 such that the shield 10 follows the axial movement of the cap 50. A stop for the distal movement of the shield 10 can be provided.

Once the cap 50 moves the shield 10 axially the cleaning chamber 20 is generated and a vacuum is automatically created in the cleaning chamber 20 such that liquid drug is sucked into the cleaning chamber 20 from the cartridge 60 once the hub 40 is moved proximally such that the proximal part 33 of the needle cannula 30 penetrates into the cartridge 60.

The housing 2 can further be provided with a further stop 4 which stops the axial movement of the cap 50 in a pre-determined position preferably defining the length of the cleaning chamber 50.

A further embodiment according to the invention is disclosed in the FIGS. 5 to 17. The same numbering is utilized for this embodiment, however with a "1" in front of the numerals.

The distal part of the housing 102 supports a protective cap 150. Further embedded in the housing 102 is the cartridge 160. The cartridge 160 is proximally sealed by the movable plunger 161 and distally by a septum 162 to be penetrated by the proximal part 133 of the needle cannula 130.

The proximal part of the housing 102 contains the piston drive system 170 which during injection drives the piston rod 171 forward to press the plunger 161 further into the interior of the cartridge 160 as is known from the prior art. In one example the piston rod 171 has a longitudinal thread 172 such that the piston rod 171 can be screwed forward by the piston rod drive system 170.

Distally the distal tip 132 of the needle cannula 130 is covered by a telescopically movable shield 110.

The telescopically movable shield 110 carries the cleaning chamber 120 formed between the outer part 123 and the slidable piston 124. Proximally the cleaning chamber 120 is bordered by a pierceable distal septum 122.

FIG. 5-5A discloses the injection device 101 as it is stored and delivered to the user. The cleaning chamber 120 is sterilized and empty and the proximal part 133 of the needle cannula 130 is held in a position outside the septum 162 of the cartridge 160. In this position no liquid communication between the interior of the cartridge 160 and the lumen 134 of the needle cannula 130 has been established.

In order to transfer liquid drug from the interior of the cartridge 160 and into the cleaning chamber 120 a transfer element 180 is provided which in response to the user rotating the protective cap 150 first applies the needle cannula 130 to the cartridge 160 and thereafter automatically transfers the correct amount of liquid drug from the cartridge 160 and into the cleaning chamber 120. This transfer element 180 is to be further explained.

Figure 6:
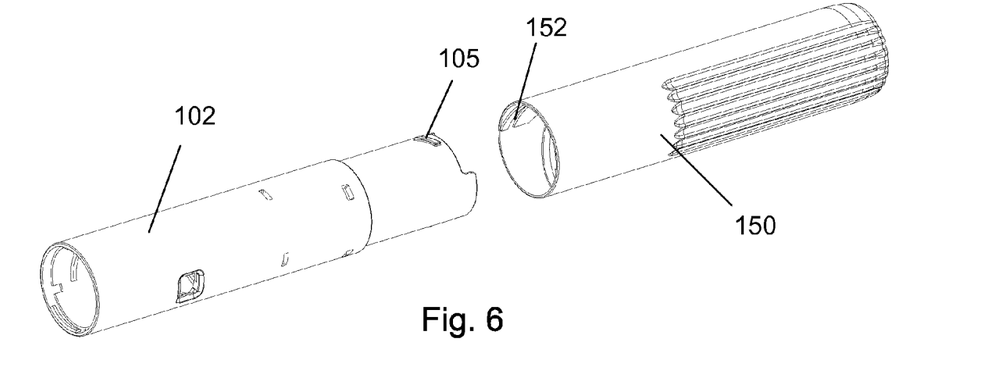
FIG. 6 show a perspective view of the engagement between the protective cap and the housing.

The connection between the housing 102 and the protective cap 150 is disclosed in FIG. 6. The housing 102 is on an exterior surface provided with a thread segment 105 which is engaged by an internal thread 152 such that the user is forced to rotate the protective cap 150 relatively to the housing 102 in order to remove the cap 150 prior to performing an injection.

FIG. 7 depicts a perspective view of the distal end of the injection device 101 with the proximal part 131 of the needle cannula 130 penetrated through the septum 162 of the cartridge 160. This penetration is performed automatically when the user rotates the protective 150 relatively to the housing 102 in the threaded connection 105/152.

For that purpose, the protective cap 150 is provided with an internally rib 153 engaging an outwardly pointing protrusion 111 located on the shield 110, such that whenever the user rotates the protective cap 150, this rib 153 translates rotation to the shield 110.

This is further disclosed in FIG. 8 which is a view through the line Z-Z in FIG. 5A where it is seen that rotation of the protective cap 150 in an anti-clockwise direction as indicated by the arrow "B" also rotate the shield 110 in an anti-clockwise direction.

Internally the shield 110 is provided with an inwardly pointing rib 112 as best seen in FIG. 9. This rib 112 abuts a flange 142 provided as an extension on the hub 140.

Figure 10:
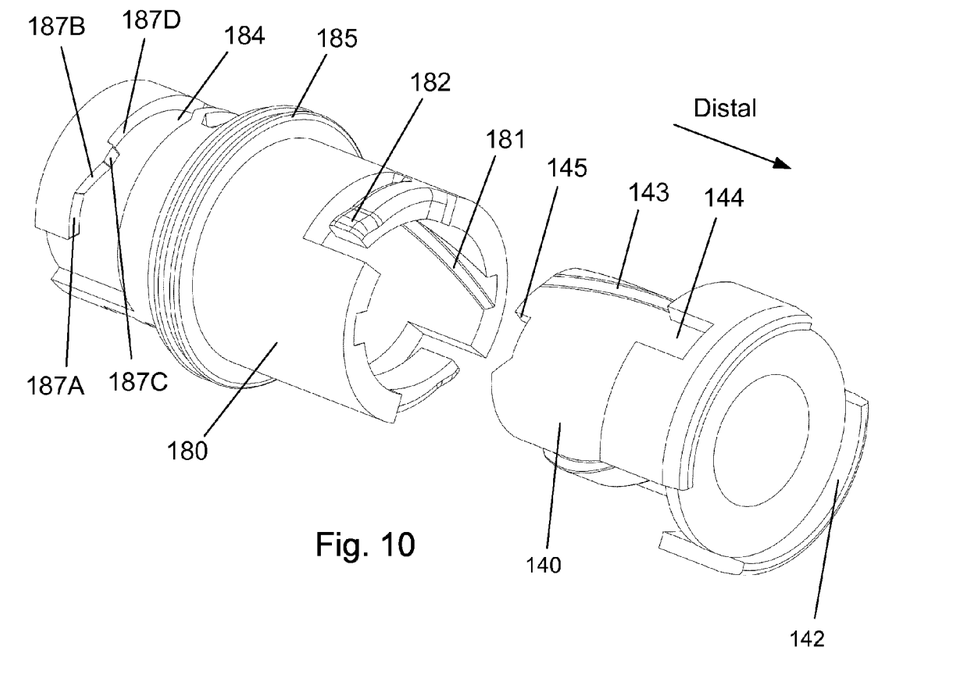
FIG. 10 show an exploded view of the engagement between the transfer element and the hub.

Further as disclosed in FIG. 10, the hub 140 holding the needle cannula 130 (not shown in FIG. 10) is externally provided with a helical thread 143 engaging an internal thread 181 provided in the transfer element 180.

As a result of the user rotating the protective cap 150, the needle hub 140 is thus screwed in the proximal direction in the threaded connection 181/143 and the proximal part 133 of the needle cannula 130 penetrates through the septum 162 and into the cartridge 160 as disclosed in FIG. 7.

Figure 11:
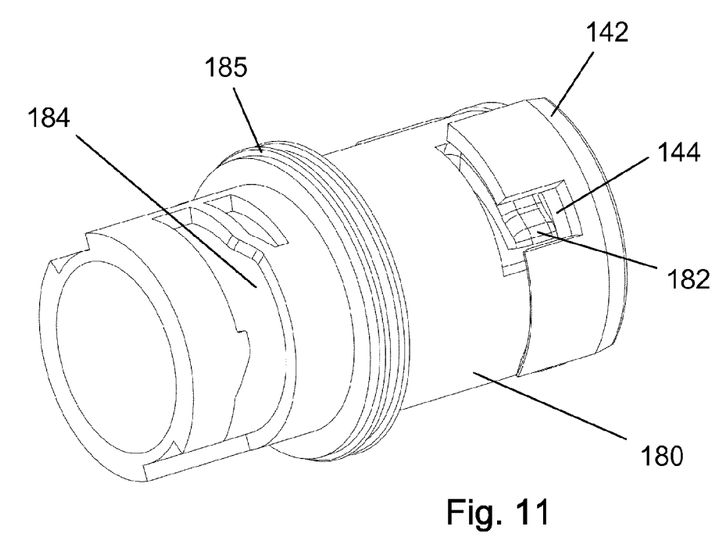
FIG. 11 show a perspective view of the engagement between the transfer element and the hub.

Once the hub 140 reaches its final proximal destination as disclosed in FIG. 7 and in FIG. 11 and the proximal part 133 of the needle cannula 130 has penetrated through the septum 162, the click-arm 182 on the transfer element 180 engages an opening 144 provided in the part of the hub 140 carrying the flange 142. This engagement secures that the hub 140 cannot rotate in the clock-wise direction (opposite "B") as this would remove the proximal part 131 of the needle cannula 130 from the cartridge 160. In this way it is secured that once the proximal part 133 of the needle cannula 130 has been penetrated through the septum 162 and into the cartridge 160 it cannot be removed from this position.

FIG. 11 further discloses a track 184 provided in an external surface of the transfer element 180, the use of which will be explained later. Further, the transfer element 180 has at least one outwardly pointing sealing rib 185, e.g. formed as a separate rubber sealing or moulded together with the transfer element 180, e.g. in a 2K moulding.

Figure 12:
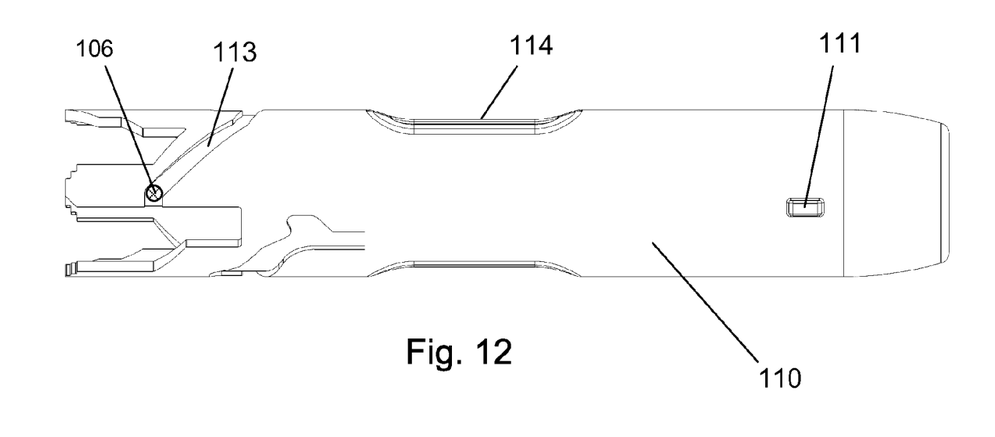
FIG. 12 show a view of the engagement between the housing and the shield.

FIG. 12 depicts the engagement between the shield 110 and the housing 101. When the user rotates the protective cap 150, the shield 110 rotates with the protective cap 150 due to the engagement with the protrusion 111 as explained. During this rotatable movement, the shield 110 also moves in the proximal direction in a helical movement since a helical groove 113 in the shield 110 is engaged by a guiding protrusion 106 provided in the housing 101. This helical groove 113 is also disclosed in e.g. FIG. 5. FIG. 12 further disclose two windows 114 in shield 110 making it possible for a user to inspect the content of the cartridge 160 before performing an injection.

The shield 110 is urged in a distal direction by a compression spring S2 which is encompassed between the housing 102 and a support element 115 supporting the proximal end of the shield 110.

Figure 13:
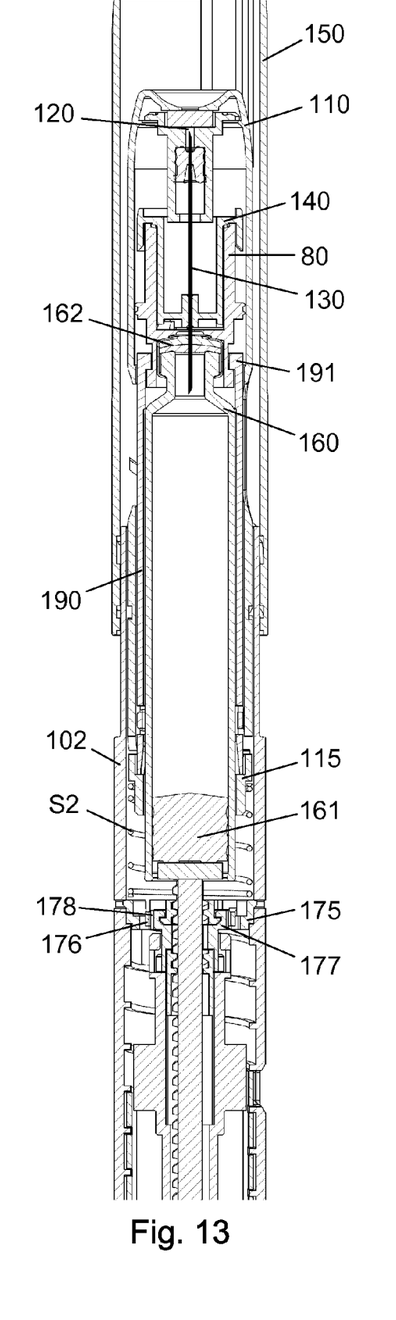
FIG. 13-13A show a cross-sectional view of the injection device with the needle cannula inserted in the cartridge.
Figure 13A:
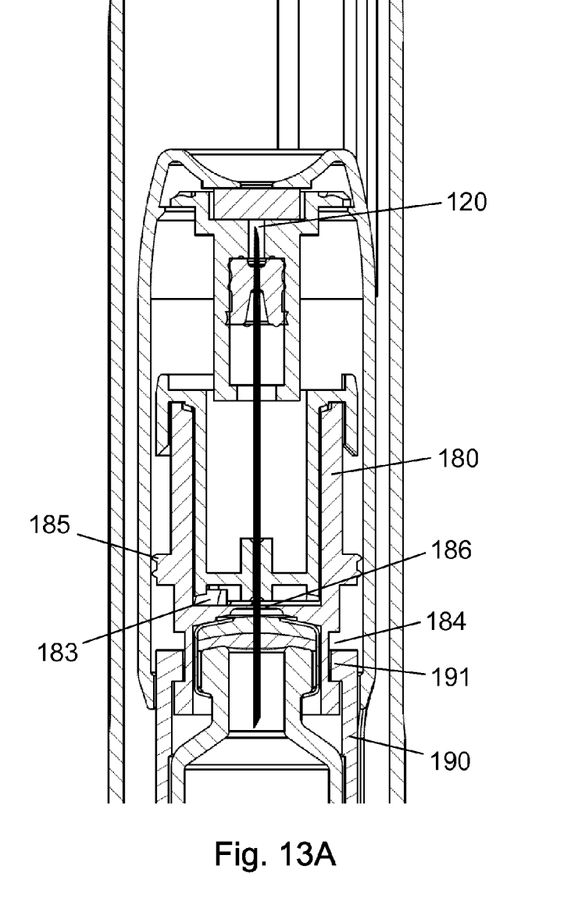

The perspective view of FIG. 7 is further disclosed in FIGS. 13-13A in which liquid communication is now established such that liquid drug can flow from the interior of the cartridge 160, through the lumen 134 of the needle cannula 130 and into the user as the plunger 161 is moved forward inside the cartridge 160 by the piston rod 171 driven by the piston rod drive system 170. Further, the hub 140 is locked to the transfer element 180 by the engagement between the click-arm 182 and the opening 144 such that the needle cannula 160 cannot be pulled out from the cartridge 160.

Once the proximal part 133 of the needle cannula 130 is properly inserted into the cartridge 160, the cleaning chamber 120 must be filled with liquid drug from the cartridge 60. This is done by further rotating the protective cap 150, the shield 110, the hub 140 and the transfer element 180 together.

The hub 140 which secures the needle cannula 130 is proximally provided with a push surface 145 which is best seen in FIG. 5A and in FIG. 10. Once the hub 140 is rotated to its proximal position this push surface 145 at the end of its helical travel abuts a similar surface structure 183 provided on the transfer element 180. Thus in a length equal to the lengthwise extension of the engagement 145/183, the transfer assembly 180 rotates together with the hub 140.

Further, a not-shown locking mechanism can be provided which ensures that the transfer element 180 can only rotate when the hub 140 has been moved proximally, this is to ensure that the filling of the cleaning chamber 120 can first be initiated when the proximal part 133 of the needle cannula 130 is fully inserted into the cartridge 160 to prevent that air is sucked into the cleaning chamber 120.

As e.g. disclosed in FIG. 13, the housing 102 comprises an internal tube structure 190 in which the cartridge 160 is slidable positioned. This tube structure 190 is further depicted in a cut-open view in FIG. 14.

This tube structure 190 can either be a separate part connected to the housing 102 or it can be moulded as an integral part of the housing 102. At the distal end the tube structure 190 has an inwardly pointing protrusion 191 which is best seen in the cut-open view in FIG. 14.

Figure 14:
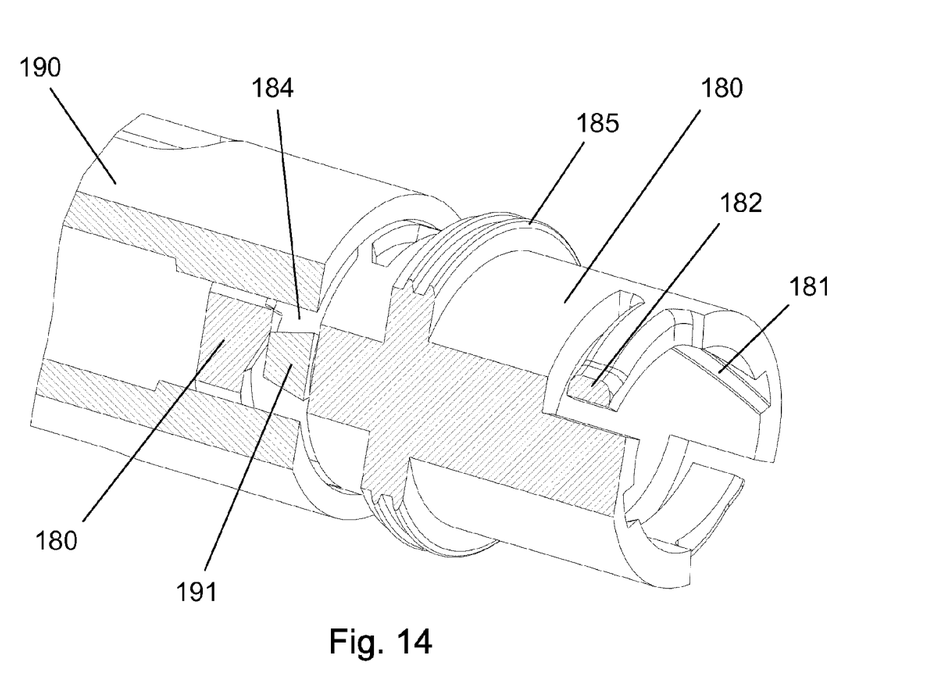
FIG. 14 show a cut-open view of the engagement between the transfer element and the housing.

This inwardly pointing protrusion 191 slides in the track 184 provided in the transfer assembly 180 such that when the transfer element 180 rotates together with the hub 140, the track 184 moves relatively to the protrusion 191.

FIG. 13 and FIG. 13A illustrates the position after the proximal part 133 of the needle cannula 130 has penetrated through the septum 162 but before the transfer element 180 starts to rotate. In this position the cleaning chamber 120 remains empty.

The transfer element 180 is provided with a sealing rib 185 which slides tightly against an inside surface of the shield 110. This sealing rib 185 makes it possible to maintain the needle cannula 130 in a sterile interior when the injection device 101 is delivered to the user. This is best seen in FIG. 5A which also discloses that the transfer element 180 making up the proximal part of the sterile interior is provided with a thin film 186 which in FIG. 13A is penetrated by the proximal part 133 of the needle cannula 130.

This thin film 186 can in one example be moulded in a 2K moulding or it can be a separate foil, e.g. made from a suitable polymer or from paper.

Further, as illustrated in FIG. 5A, the inside surface of the shield 110 is dislocated i.e. has a larger diameter in the distal region such that when the shield 110 is moved proximally as the shield 110 moves helically due to the track 113, the sealing rib 185 slides into an area with the larger diameter since the sterile interior is not needed anymore once the proximal part 133 of the needle cannula 130 has been pushed through the septum 162 and into the cartridge 160 as disclosed in FIGS. 13-13A.

As seen in FIG. 10 and FIG. 14, the proximal sidewall of the track 84 comprises four different regions 187A, 187B, 187C, 187D which moves the transfer element 180 in the proximal direction in relation to the tube structure 190 as the transfer element 180 rotates and the protrusion 191 shifts between the regions 187 A, B, C, D.

In the position disclosed in FIG. 13 and FIG. 13A the protrusion 191 rest against the first region 187A of the sidewall. When the transfer element 180 with the track 184 rotates, the protrusion 191 is lifted via the sloped region 187B up to the third region 187C. Since the protrusion 191 is a part of the housing 101 via the tube structure 180, the transfer assembly 180 is moved in the proximal direction relatively to the housing 102.

The transfer element 180 further abuts the distal end of the cartridge 160 as e.g. disclosed in FIG. 13A such that when the transfer element 180 is forced proximally, the cartridge 160 is also forced to move proximally inside the tube structure 190 forming part of the housing 102.

The piston rod 171 is in the piston rod drive system 170 secured against any backward movement as it is common in pre-filled injection devices. This can e.g. be made by providing the piston rod drive system with a one-way ratchet.

Figure 15:
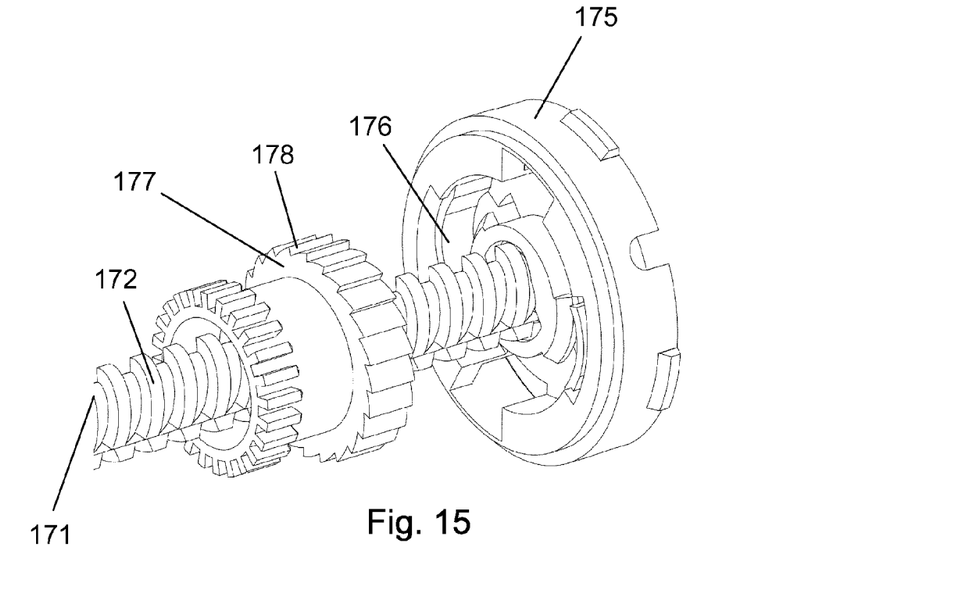
FIG. 15 show a perspective view of the one way mechanism.

This is disclosed in FIG. 15 which discloses a first drive part 175 secured in the housing 102 (see e.g. FIG. 13) and a second drive part 177 to be rotated during injection. The rotation of the second drive part 177 is preferably done by a spring such as a torsion spring. One of the first part 175 or the second part 177 is keyed to the piston rod 171 whereas the other part is threaded to the piston rod 171 such that when the first part 175 and the second part 177 is rotated relatively to each other the piston rod 171 is driven in the distal direction with or without rotating.

In the disclosed embodiment, the first part 175 is provided with at least one ratchet arm 176 engaging a toothed outer surface 178 on the second part 177 such that the first part 175 and the second part 177 can only be rotated relatively to each other in one rotational direction thus being the direction that moves the piston rod 171 distally.

As the piston rod 171 is prevented from backward movement so is the plunger 161 inside the cartridge 160 as the plunger 161 abuts the piston rod 171 e.g. via a piston rod foot distributing the force. Proximal movement of the cartridge 160 with the plunger 161 remaining in its position builds up a pressure in the interior of the cartridge 160.

This pressure inside the cartridge 160 is build up as the protrusion 191 moves from the first region 187A to the third region 187C via the second region 187B, however, once the protrusion 191 reaches the fourth region 187D, the pressure is somewhat relieved since the fourth region 187D lies more proximal than the third region 187C. However, the fourth region 187D lies a little more distal than the first region 187A. The result being that the pressure increase going from the first region 187A to the third region 187C pumps out a quantum of drug from the cartridge 160 in order to start the piston 124 inside the cleaning chamber 120 to move where after the pressure build-up is reduced a little by going into the fourth region 187D.

Figure 16:
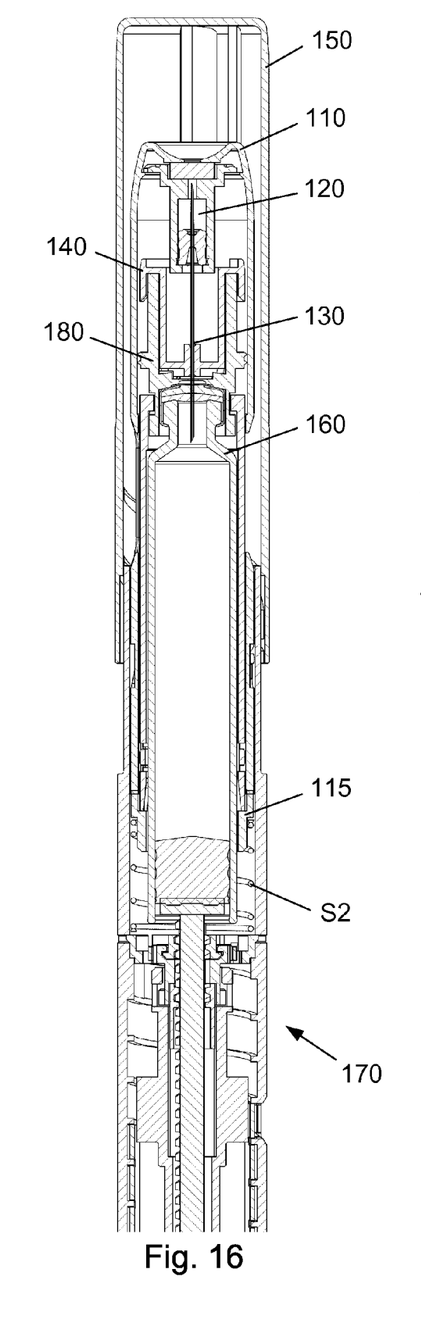
FIG. 16-16A show cross-sectional views of the injection device with the cleaning chamber filled.
Figure 16A:
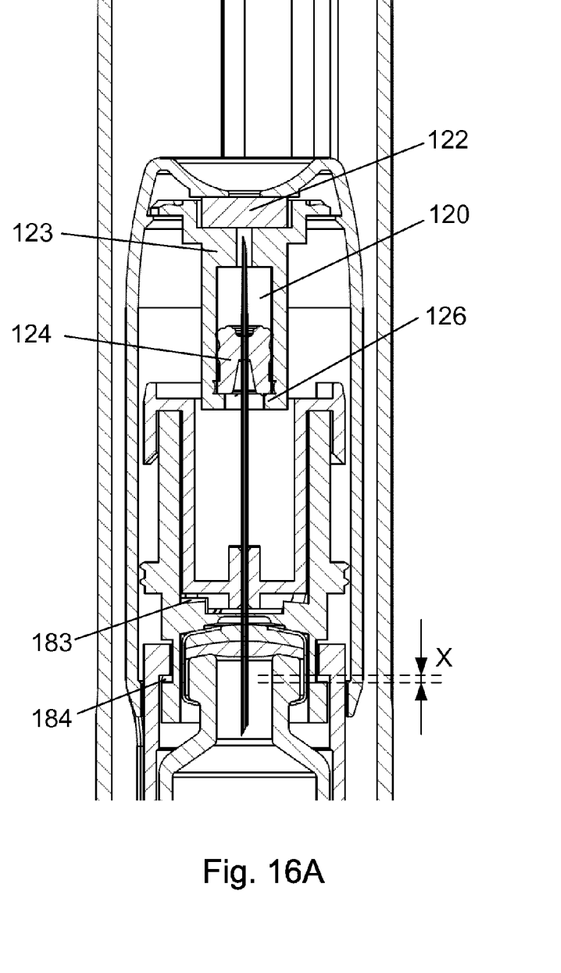

This situation wherein the protrusion 191 is in the fourth region 187D is disclosed in FIGS. 16-16A. As the transfer element 180 moves proximally a distance "X", so does the cartridge 160 whereby the pressure build-up forces a pre-determined amount of the liquid drug inside the cartridge 160 to flow through the lumen 134 of the needle cannula 130 and into the cleaning chamber 120.

As the cleaning chamber 120 is filled, the piston 124 is moved proximally until it abut the stop surface 126 as best seen in FIG. 16A. This is further depicted in a perspective view in FIG. 17 in which the injection device 101 is ready to use.

Figure 17:
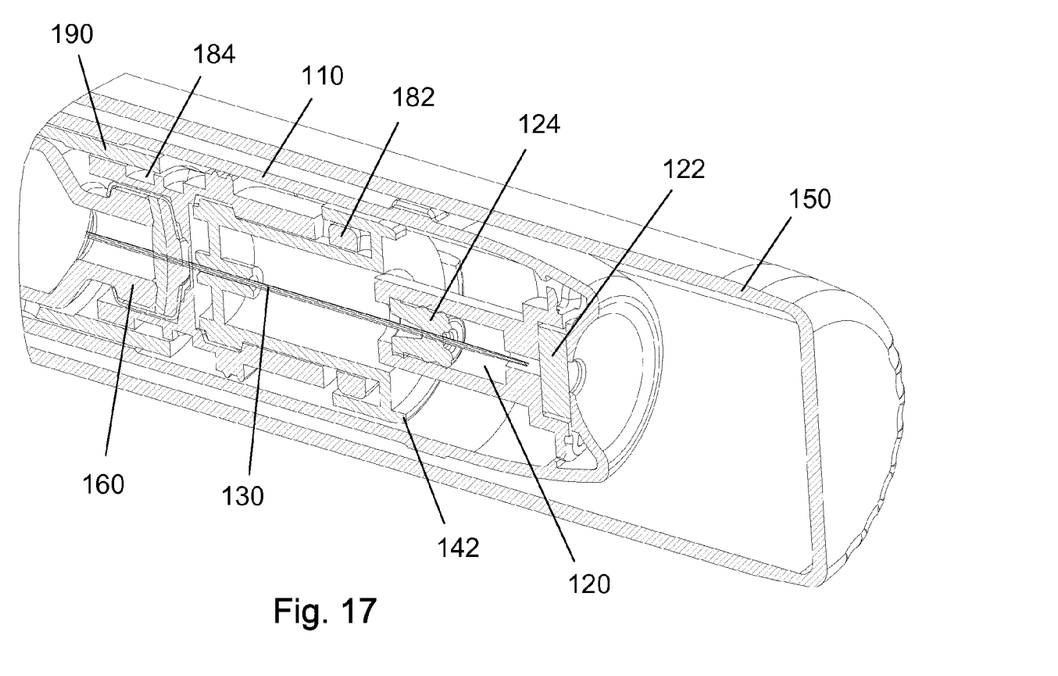
FIG. 17 show a perspective view of FIG. 16A.

When an injection is to be performed, the user dials a dose using a dose setting button provided at a proximal end of the injection device 101. This rotation strains a torsion spring which is released to drive the piston rod 171 forward. Before releasing the torsion spring, the user removes the protective cap 150 and presses the distal end of the shield 110 against the skin such that the distal tip 132 of the needle cannula 130 penetrates through the distal septum 122 and into the skin of the user where after the torsion spring and thus the injection is released.

When the end of the shield 110 is removed from the skin after the injection, the compression spring S2 urges the shield 110 back to its extended position such that the distal tip 132 of the needle cannula 130 is brought back into the cleaning chamber 120 wherein the distal tip of the needle cannula 130 is maintained between injections.

Example of a Pharmaceutical Preservative Containing Liquid Drug:

In one specific example, the liquid pharmaceutical preservative containing drug contained in the interior of the cartridge 160 and in the cleaning chamber 120 of the telescopic shield 110 could be NovoLog®, which is manufactured and sold by the Danish company Novo Nordisk A/S.

NovoLog® is a sterile, aqueous, clear, and colourless solution that contains:
insulin aspart 100 Units/mL
glycerin 16 mg/mL
phenol 1.50 mg/mL
metacresol 1.72 mg/mL
zinc 19.6 mcg/mL
disodium hydrogen phosphate dehydrate 1.25 mg/mL
sodium chloride 0.58 mg/mL
water for injection NovoLog has a pH of 7.2-7.6 and Hydrochloric acid 10% and/or sodium hydroxide 10% may be added to adjust pH.

The preservatives (phenol and metacresol) are simultaneously present both in the cartridge 160 and in the cleaning chamber 120 of the telescopic shield 110. Since the liquid inside the interior of the cartridge 160 and inside the cleaning chamber 120 are the same pharmaceutical preservative containing liquid drug, the exchange of liquid through the lumen 134 of the needle cannula 130 has no influence on the pharmaceutical preservative containing liquid drug to be injected as only the identical same pharmaceutical preservative containing liquid drug is present inside the cartridge 160 and in the cleaning chamber 120 of the telescopic shield 110 thus no contamination is possible.

Some preferred embodiments have been shown in the foregoing, but it should be stressed that the invention is not limited to these, but may be embodied in other ways within the subject matter defined in the following claims.

The invention claimed is:

1. A pre-filled injection device for apportioning set dose of a liquid drug comprising:
a housing distally supporting a removable protective cap rotatable mounted on the housing, and which housing proximally supports a piston rod drive system,
a non-replaceable cartridge embedded in the housing of the pre-filled injection device and having an interior containing a liquid preservative containing drug, the cartridge having a movable plunger with a proximal surface abutting the piston rod drive system which comprises a piston rod, for moving the movable plunger in the distal direction wherein the piston rod is prevented from movement in the proximal direction by a one-way ratchet,
a needle cannula having a distal part with a distal tip and an opposite proximal part and a lumen there between,
a telescopically movable shield movable from an extended position covering at least the distal tip of the needle cannula to a retracted position exposing at least the distal tip of the needle cannula, and which telescopically movable shield carries a cleaning chamber for containing a cleaning solvent for cleaning at least the distal tip of the needle cannula between subsequent injections, wherein the cleaning chamber has a variable volume and comprises a movable piston operating inside the cleaning chamber,
wherein the cleaning solvent inside the cleaning chamber when filled, is identical to the liquid preservative containing drug contained in the interior of the cartridge and wherein the liquid preservative containing drug is filled into the cleaning chamber through the lumen of the needle cannula by moving the movable plunger and the cartridge relatively to each other,
and wherein a transfer assembly is provided for transferring rotation of the removable protective cap to an axial displacement of the cartridge in the proximal direction and wherein the plunger is proximally supported by the piston rod and prevented from moving in the proximal direction,
wherein the transfer assembly comprises a transfer element engaging a hub which carries the needle cannula and wherein the transfer element and the hub are coupled by a threaded connection, wherein the transfer element moves proximally when rotated,
such that the liquid preservative containing drug is forced from the cartridge and into the cleaning chamber as the transfer element moves the cartridge in the proximal direction and the plunger is prevented from movement in the proximal direction.

2. A pre-filled injection device according to claim 1, wherein the removable protective cap is provided with a structure for translating rotation of the removable protective cap to rotation of the shield.

3. A pre-filled injection device according to claim 2, wherein the shield is provided with a structure for translating rotation of the shield to a rotation of the hub.

4. A pre-filled injection device according to claim 3, wherein the hub when rotated screws proximally in the threaded connection.

5. A pre-filled injection device according to claim 3, wherein the hub is provided with a structure for translating rotation of the hub to a rotation of the transfer element.

6. A pre-filled injection device according to claim 5, wherein the transfer element is helically guided in the housing.

7. A pre-filled injection device according to claim 6, wherein the housing is provided with a protrusion engaging a track provided in the transfer element.

8. A pre-filled injection device according to claim 7, wherein the protrusion is provided in a tube structure forming part of the housing.

9. A pre-filled injection device according to claim 1, wherein the transfer element abuts the cartridge such that the cartridge follows the proximal movement of the transfer element.

10. A pre-filled injection device according to claim 1, wherein the cleaning chamber is formed between a distal septum and a piston being movable mounted in an outer part secured to the shield.

* * * * *